United States Patent [19]

Berens

[11] Patent Number: 5,936,109

[45] Date of Patent: Aug. 10, 1999

[54] LIGANDS FOR ASYMMETRIC CATALYSIS

[75] Inventor: Ulrich Berens, Cambridge, United Kingdom

[73] Assignee: Chirotech Technology Limited, United Kingdom

[21] Appl. No.: 08/893,105

[22] Filed: Jul. 15, 1997

[30] Foreign Application Priority Data

Jul. 15, 1996 [GB] United Kingdom .................... 9614857
Apr. 18, 1997 [GB] United Kingdom .................... 9707582

[51] Int. Cl.$^6$ ................................ C07F 9/02; C07F 15/00
[52] U.S. Cl. .............................. 556/14; 556/20; 556/136; 568/12
[58] Field of Search ................................. 556/14, 20, 136; 568/12; 560/51, 155

[56] References Cited

U.S. PATENT DOCUMENTS

| 5,008,457 | 4/1991 | Burk | 568/12 |
| 5,171,892 | 12/1992 | Burk | 568/12 |
| 5,532,395 | 7/1996 | Burk | 556/18 |

FOREIGN PATENT DOCUMENTS 9802445  1/1998  WIPO.

OTHER PUBLICATIONS

Marinetti, A., L. Ricard (1993) Synthesis and Characterization of Some P–Menthylphosphetanes, a New Class of Electron–Rich Chiral Phosphines. Tetrahedron 49(45): 10291–10304.

Marinetti, A., L. Ricard (1994) Phosphetanes as Chiral Ligands for Catalytic Asymmetric Reactions: Hydrosilylation of Olefins. Organometallics 13: 3956–3962.

William Tumas, Organometallics, vol. 11, No. 8, pp. 2944–2947, 1992.

*Primary Examiner*—Porfirio Nazario-Gonzalez
*Attorney, Agent, or Firm*—Saliwanchik, Lloyd & Saliwanchik

[57] ABSTRACT

The subject invention relates to phosphine ligands that are useful for asymmetric reactions, especially as chiral ligands for catalytic asymmetric hydrogenation.

26 Claims, No Drawings

LIGANDS FOR ASYMMETRIC CATALYSIS

FIELD OF THE INVENTION

This invention relates to phosphine ligands that are useful for asymmetric reactions, especially as chiral ligands for catalytic asymmetric hydrogenation.

BACKGROUND OF THE INVENTION

Chiral phosphines are useful ligands for asymmetric catalysis. In particular, ligands incorporating a trans-2,5-disubstituted phospholane of formula (1), or the opposite enantiomeric form (2)

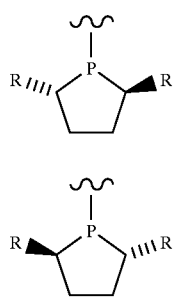

wherein R is linear or branched alkyl, are effective for rhodium and ruthenium-catalysed asymmetric hydrogenation. Bidentate phosphine ligands of this type, typified by methyl-DUPHOS, are disclosed in U.S. Pat. Nos. 5,008,457, 5,177,230, 5,206,398 and 5,322,956.

These phospholane ligands provide good stereocontrol in the hydrogenation of a broad range of substrate types (for a review, see Burk et al, Pure Appl. Chem. (1996) 68:37–44). For example, hydrogenation of enamides provides amino-acid derivatives in high enantiomeric excess; see Burk et al, J. Am. Chem. Soc. (1993) 115:10125. Chiral alcohols can also be produced by these ligands in high optical purity; see Burk et al, J. Am. Chem. Soc. (1995) 117:4423.

Although the 5-membered ring phospholane ligands are useful in asymmetric synthesis, the ligands themselves are difficult to synthesise. This can be a limitation to their usage on an industrial scale, and arises from the need to synthesise the chiral, 1,4-diol intermediate which is required for construction of the 5-membered ring; see Burk et al, Organometallics (1990) 9:2653, U.S. Pat. Nos. 5,021,131 and 5,329,015. This requires specialist methods such as an electrochemical Kolbe coupling which can be problematic on scale-up.

The chiral, 1,4-diols are otherwise difficult to access. For example, 1,4-diketones are difficult to hydrogenate under asymmetric catalytic conditions, giving low yields of poor optical purity material and producing mainly the achiral meso-1,4-diol.

Phosphetanes have been prepared by reaction of organophosphorus reagents with olefins (Marinetti et al, Tetrahedron (1993), 49:10291) or by alkylation of phosphine complexes with an alkyl halide (Hockless et al, Organometallics (1996) 15:1301). The latter method leads to extensive polymer formation.

SUMMARY OF THE INVENTION

Novel compounds according to this invention are chiral phosphetanes of the formulae

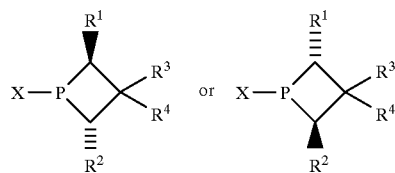

wherein X is a group that forms a stable bond to phosphorus. X may include a further phosphetane ring, in which case compounds of the invention have the formula:

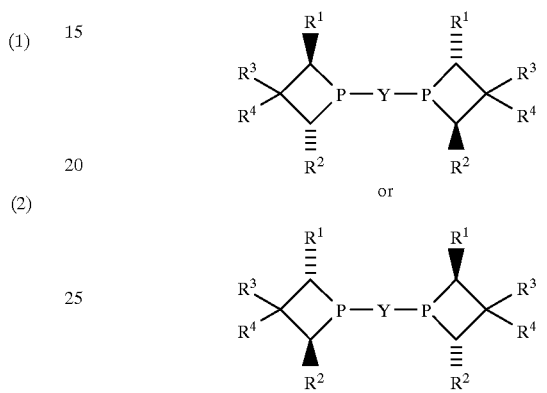

wherein Y is a bivalent group capable of forming stable bonds to phosphorus. $R^1$, $R^2$, $R^3$ and $R^4$ are each H, alkyl, cycloalkyl, aryl or aralkyl.

These phosphetanes, which are easily accessible from readily available 1,3-diol precursors, are ligands which may be complexed with a transition metal such as iridium, rhodium and ruthenium to provide a catalyst for asymmetric synthesis, especially asymmetric hydrogenation. One aspect of the present invention is the surprising discovery that the performance of such catalysts can surpass that of equivalent catalysts derived from homologous phospholane ligands.

DESCRIPTION OF THE INVENTION

The group attached to the phosphetane, X or Y, may be any such residue which forms a stable bond to phosphorus. In particular, this may be an organic alkyl or aryl group, a heterocyclic group, or an organometallic residue such as ferrocenyl. It may have up to 8, 12 or 20 C atoms.

For the monodenatate compounds, X is preferably phenyl. For the bidentate compounds, Y is preferably 1,2-phenylene or —$(CH_2)_{1-6}$—, e.g. —$CH_2$—.

The substituents at the chiral centre of the phosphetane $R^1$ and $R^2$ are preferably the same, and are preferably each a lower alkyl group, especially methyl, ethyl and isopropyl, but may also be aryl or cycloalkyl, e.g., fluoroalkyl, it may be substituted, without affecting utility. Each may have up to 8, 10 or 12 C atoms. $R^3$ and $R^4$ are preferably hydrogen, but may also each be groups of the same scope as $R^1$. Optionally, $R^3$ and/or $R^4$ can be joined to either of $R^1$ and $R^2$ to form a ring.

By way of example, the chiral phosphetanes of the invention may be monodentate ligands such as (3), or bidentate ligands such as (4) and (5). For asymmetric hydrogenation reactions at least, such chiral phosphetanes are particularly useful.

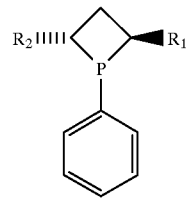

(3)

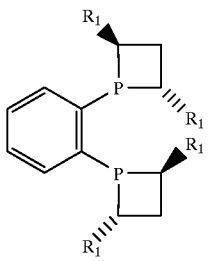

(4)

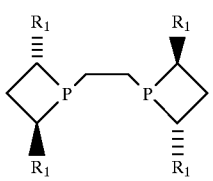

(5)

The utility of the present invention can be demonstrated by the effectiveness of the rhodium-based catalyst derived from the monodentate ligand (3) wherein $R^1=R^2=Me$, relative to catalyst derived from the phospholane homologue, described by Burk, Organometallics (1990) supra. The results of these studies, concerning the asymmetric hydrogenation of 4 classes of functionally distinct substrates, are shown below, in Table 1. As can quickly be discerned, in each case the phosphetane-containing catalyst outperformed the phospholane-catalyst with regard to enantioselectivity.

In addition, Table 1 shows that the desired effect is demonstrable with acetophenone, even though this is not recognised as a satisfactory substrate for such reactions.

Chiral 1,3-diols that can be used as starting materials for the preparation of the novel phosphetanes are readily available. They can be prepared in very high optical purity by asymmetric hydrogenation of the corresponding 1,3-diketones. For example, Noyon et al, J. Am. Chem. Soc. (1988), 110:629, discloses the preparation of (R,R)-2,4-pentanediol by utilisation of Ru-BINAP as catalyst. It has been found that this method is also applicable to other chiral 1,3-diols, for example (3R, 5R)-2,6-dimethyl-3-5-heptanediol, the precursor to phosphetanes wherein both $R^1$ and $R^2$ are isopropyl. For preparation of the Ru-BINAP catalyst, the method of Heiser was prepared, as described in Tetrahedron Asymmetry (1991) 2:51. The 1,3-diketone precursors are either commercially available, or may be conveniently prepared according to the method of Brändström, Ark. Kemi (1951/52) 38:365. The ability to prepare chiral phosphine ligands directly from the readily-available chiral 1,3-diols makes these phosphetanes particularly attractive for use in large-scale industrial applications.

The conversion of a chiral 1,3-diol to a chiral phosphetane is exemplified by the synthesis of the 1-phenylphosphetane (3), outlined in the following Scheme:

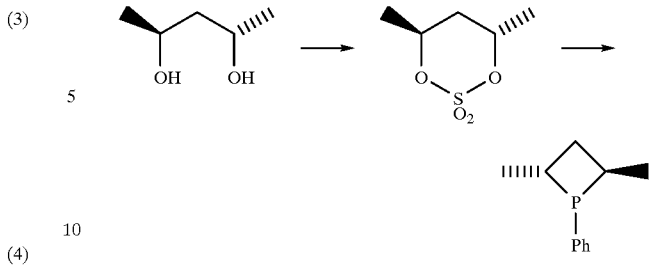

In this scheme, the chiral 1,3-diol pentane-2,4-diol is firstly converted to its cyclic sulfate which is then treated with lithium phenylphosphide, followed by a second lithiation with butyllithium, to form the cyclic phosphetane. The general utility of this process, to prepare any compound of the invention, will be readily apparent to those of ordinary skill in the art. Thus, for example, phosphetanes of the invention can be prepared via lithiation of $XPH_2$.

The method described herein represents a novel approach to the synthesis of phosphetanes and has the added advantage that any polymerised material is formed in the reaction can be easily removed by distillation.

The following Examples illustrate the preparation and utility of products of the invention.

EXAMPLE 1

(4S,6S)-4,6-Dimethyl-2,2-dioxo-1,3,2-dioxathiane a) (4S,6S)-4,6-dimethyl-2-oxo-1,3,2-dioxathiane (cyclic sulfite). A solution of thionyl chloride (14.3 g, 0.12 mol) in dichloromethane (60 ml) is dropped within ten minutes to neat (2S,4S)-pentanediol-2,4(10.4 g, 0.1 mol). The obtained yellow solution is stirred for another ten minutes and then the solvent is removed on a rotavapor to leave the product. $^1$H-NMR (200 MHz, CDCl$_3$): δ 13.7, 1.55 (2 d, * 3 H, 2 CH$_3$), 1.85–2.20 (m, 2 H, CH$_2$) 4.45 ('sext', 1 H, CH), 5.03 (m, 1 H, CH) $^{13}$C-NMR (50 MHz, CDCl$_3$); δ 20.67, 22.27 (2 CH$_3$); 37.76 (CH$_2$); 62.16, 71.47 (2 CH).

b) (4S,6S)-4,6-dimethyl-2,2-dioxo-1,3,2-dioxathiane (cyclic sulfate). The material obtained from a) was redissolved in a mixture of dichloromethane (60 ml) and acetonitrile (60 ml). A solution of RuCl$_3$—xH$_2$O (200 mg) in water (100 ml ) was added. The obtained brown biphasic mixture was cooled to 0° C., and then NaIO($_4$) (32.1 g, 0.15 mol) was added in one portion. Within two minutes the temperature had risen to 25° C., and the colour had turned from dark to pale brown. After stirring the mixture for another hour the organic layer was separated and washed with 10% sodium sulfite solution (200 ml). Pentane (ca 200 ml) was added, and then the isolated organic layer was dried (Na$_2$SO$_4$). After removal of the solvent the product was obtained as mobile colourless liquid which crystallised. Yield 14.3 g (86%). $^1$H-NMR (200 MHz, CDCl$_3$): δ 1.60 (d, 6 H, CH$_3$), 2.05 ('tr', 2 H, CH$_2$), 5.08 ('sext', 2 H, CH). $^{13}$C-NMR (50 MHz, CDCl$_3$): δ 19.72 (CH$_3$), 35.03 (CH$_2$), 80.18 (CH).

EXAMPLE 2

(2R,4R)-2,4-Dimethyl-1-phenylphosphetane

A 100 ml Schlenk flask was purged with N$_2$ and then charged with anhydrous ether (25 ml) and phenylphosphine (1.1 g, 10 mmol). Then 4.0 ml of a 2.5 molar solution of n-BuLi was slowly added via a syringe. The obtained yellow solution of lithium phenylphoshide was stirred for 10 minutes and then a solution of 1.66 g (10 mmol) of (4S, 6S)-4,6-dimethyl-2,2-dioxo-1,3,2-dioxathioxane in 20 ml of THF was added dropwise over a period of 20 minutes. When the addition was complete, 5 ml of THF was added to dissolve the oily material and then a solution (4.0 ml) of 2.5 molar n-BuLi, which was diluted with 10 ml of pentane, was added dropwise under efficient stirring to the reaction mixture over a period of 45 minutes. The reaction was then stirred for a further 15 minutes, and then the solvent was removed in vacuo. The residue was treated with pentane (ca. 10 ml), the precipitated salt removed by filtration, and the filter cake washed with pentane (ca. 10 ml). Evaporation of the solvent from the filtrate gave a colourless oil which consisted of a 75:25 mixture of (2R,4R)-2,4-dimethyl-1-phenylphosphetane and polymer.

$^{13}$C-NMR(C$_6$D$_6$, 50 MHz): δ 17.82 (CH$_3$, $^2J_{P,C}$=4.8 Hz) 20.54 (CH$_3$, $^2J_{P,C}$=22.3 Hz), 24.36 (CH, $^1J_{P,C}$=3.8 Hz), 25.09 (CH, $^1J_{P,C}$=8.2 H) 39.25 (CH$_2$, $^3J_{P,C}$32 1.4 Hz), 128.0 (Ph p-C), 128.67 (Ph m-C$^3J_{P,C}$4.9=Hz), 131.95 (Ph o-C$^2J_{P,C}$32 15.0 Hz), 139.37 (Ph ipso-C$^1J_{P,C}$32 35.1 Hz), $^{31}$P-NRM (C$_6$D$_6$, 161 MHz): δ 24.28. The polymer gave a singlet at δ−13.05 ppm.

For preparation on a larger scale, phenylphosphine (5 g, 45.5 mmol) and cyclic sulfate) (7.56 g, 45.5 mmol) were reacted in a similar way, to give after distillation 1.86 g (23%) of (2R,4R)-2,4-dimethyl-1-phenylphosphetane, bp 120–124° C. at 2.4 mbar. Spectroscopic analysis indicated this material to be of >95% chemical purity.

EXAMPLE 3

Bis[(2R,4R)-2,4-Dimethyl-1-phenylphosphetano]-(1,5-cyclooctadiene)rhodium(I) tetrafluorborate All procedures were carried out under an atmosphere of nitrogen. Fluroboric acid diethyl etherate (162 mg, 1.0 mmol) was added to a solution of (R,R)-2,4-dimethyl-1-phenylphosphentane (356 mg, 2.0 mmol) in degassed THF (1.5 ml) giving a cloudy solution. This mixture was then added dropwise to a yellow solution of [Rh(COD)(acac)] (310 mg, 1.0 mmol) in degassed THF (1.5 ml). The resultant orange solution was heated at 50° C. for 10 minutes and then cooled to room temperature. Degassed diethyl ether (5 ml) was added giving an orange oil which crystallised on standing, resulting in an orange solid. The solvent was decanted off and the solid washed with THF (2 ml) which was again removed by decantation to give, after drying under vacuum, the catalyst (1) (298 mg, 45%) as an orange solid.

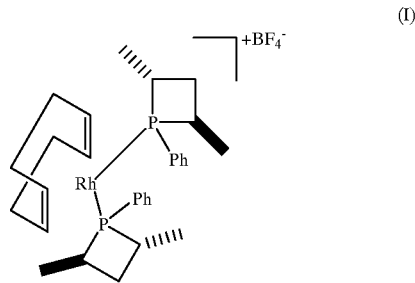

(I)

$^1$H-NMR (CDCl$_3$, 200 MHz): δ 0.56, 1.47 (2 m, 3 H each, 2 CH$_3$), 2.05–2.35, 2.35–2.65 ) (2 m, 7 H and 1 H, 2 phosphetane, CH, phosphetane CH$_2$, 2 COD-CD$_3$), 4.95–5.25 (m, 2 H, 2 COD-CH), 7.31, 7.52 (m, 2 H and 3 H, phenyl-H). $^{13}$C-NMR (CDCl$_3$, 50 MHz); δ 16.87, 18.70 (2'tr', CH$_3$), 26.80, 27.49 (2 'd', phosphetane CH), 29.89, 30.52 (2 s, COD-CH$_2$), 37.81 ('tr', phosphetane-CH$_2$) 96.54, 101.48 (2 m, 2 COD-CH), 129.05 (m, phenyl ipso-C), 128.93, 131.08, 132.24 (other phenyl-C). $^{31}$P-NMR (CDCl$_3$, 162 MHz): δ 65.69 (d, J$_{P,C}$145 Hz).

EXAMPLE 4

(3R,5R)-2,6-Dimethyl-3,5-heptanediol

The distilled mixture of 2,6 dimethyl-3,5-heptanedione and diethyl malonate obtained from the reaction of diethyl malonate (264 g) and isobutyric acid anhydride (500 g, (201 g, containing ca, 150 g of the diketone) was dissolved in 200 ml of methanol and degassed by sparging with nitrogen for 20 minutes plus the following cycles of vacuum (5 min ca. 20 mbar) and stirring under nitrogen (5 min). To this solution was added the solution of the Ru-(S)-Tol-BINAP obtained from (S)-Tol-BINAP (494 mg, 0.729 mmol) and Ru(COD) (methallyl)$_2$(212 mg, 0.66 mmol. The mixture was transferred under strict exclusion of air into a nitrogen flush 2 L Parr hydrogenation bomb. After purging the bomb with hydrogen the hydrogenation was performed at 100° C./115 bar for five hours. The solvent was removed from the reaction mixture on a rotavapor, and the residue was distilled in vacuum over a 30 cm vigreux column. Yield: 78 g, 150° C. at 26 mm, needles, mp 83–84° C. $^1$H-NMR (CDCl$_3$, 200 MHz): δ0.90, 0.96 (2 d, 12 H, $^3$J32 6.8 Hz, 2 CH$_3$); 1.59 ('dd', 2 H, CH$_2$); 1.69 (oct. 2 H, CHMe$_2$); 2.40 (br s, 2 H, OH); 3.63 ('q', 2 H, CHOH). $^{13}$C-NMR (CDCl$_3$, 50 MHz); δ16.07 18.64 (2 CH$_3$); 33.64 (CHMe$_2$); 36.47 (CH$_2$); 73.90 (CHOH).

EXAMPLE 5

(4R,6R)-4,6-Diisopropyl-2,2-dioxo-1,3,2-dioxathiane a) (4R,6R)-4,6-diisopropyl-2-oxo-1,3,2-dioxathiane (cyclic sulfite): A 500 ml flask was charged with (3R,5R)-2,6-dimethyl-3,5-heptanediol (16.02 g, 0.1 mmol) and dichloromethane (100 ml). To this solution was added thionyl chloride (14.3 g) via a syringe within 2 minutes. When the evolution of HCl had ceased stirring was stopped, and the solvent was removed on the rotavapor to leave the product as yellow oil. $^{13}$C-NMR (CDCl$_3$, 50 MHz); δ 17.52, 17.70, 18.14, 18.46 (4 CH$_3$); 31.27 (CH$_2$); 32.16, 32.63 (2 CHMe$_2$); 71.18, 78.97 (2 CHOH).

b) (4R,6R)-4,6-diisopropyl-1,3,2-dioxathiane (cyclic sulfate). The crude cyclic sulfite obtained from a) was dissolved in ethyl acetate (100 ml). To this solution was added RuCl$_3$·xH$_2$O (20 mg), crushed ice (100 g), and NaIO$_4$ (25.7 g, 0.12 mol). The mixture was stirred rapidly, and within 1½ minutes the colour had changed to yellow. The organic layer was decanted, and the aqueous layer was extracted with four portions of ethyl acetate (100 ml each). To the vigorously stirred combined organic layers was added Na$_2$SO$_3$, and stirring was continued until the colour of the organic layer had disappeared almost completely (ca. 25 min). After drying (Na$_2$SO$_4$) and filtering the solvent was removed to leave the (4R,6R)-4,6-diisopropyl-2,2-dioxo-1,3,2-dioxathiane as yellow oil which crystallised from pentane. Yield 18.6 g (83.4%). $^1$H-NRM (CDCl$_3$, 200 MHz); δ 0.97 (d, 6 Hz, CH$_3$); 1.07 (d, 6 H, J=6.6 Hz, CH$_3$); 2.08 ('tr', 2 H, CH$_2$); 2.15 (m, 2 H, CHMe$_2$); 4.45 ('quart', 2 H, OCH). $^{13}$C-NMR (CDCl$_3$, 50 MHz); δ18.02, 18.10 (2 CH$_3$); 28.81 (CH$_2$) 31.45 (CHMe$_2$), 88.03 (OCH).

EXAMPLE 6

(2S,4S)-2,4-Diisopropyl-1-phenylphosphetane

In a 100 ml Schlenk flask a solution of lithium phenylphosphanide was prepared by the slow addition of n-BuLi (10 minutes, 2.5 n solution, 28 ml, 70 mmol) via a syringe to a solution of phenylphosphine (7.7 g, 70 mmol) in THF (60 ml) at 0° C.

A solution of the cyclic sulfate (4R,6R)-4,6diisopropyl-2,2-dioxo-1,3,2-dioxathiane (16.32 g, 73.5 mmol, 5% excess) was made up in a Schlenk flask in absolute THF (700 ml), sparged with nitrogen for 30 minutes, and cooled to −78° C. The lithium phenylphosphanide solution was added to this solution via a syringe within 20 minutes. The pale yellow mixture was stirred at −78° C. for one more hour, and then the second portion of BuLi (2.5 n solution, 30 ml, 75 mmol) was added within 30 minutes to the reaction mixture. The mixture was allowed to warm up overnight, and then the solvent was distilled off. To the residue was added water (100 ml) and sulfuric acid (10 ml of 2 m acid), and the ligand was extracted from this mixture into pentane. After drying ($Na_2SO_4$) and removal of the solvent the residue (14.6 g) was double-distilled in vacuum to give the ligand as colourless liquid. Yield: 8.68 g (53% based on phenyl phosphine), bp. 120° C. at 2mbar. $^1$HNMR ($CDCl_3$, 400 MHz): δ 0.63, 0.67 (2 d, 6 H, J32 6.4 Hz, 2 $CH_3$); 1.03, 1.05 (2 d, δH, J32 6.4 Hz, 2 $CH_3$); 1.28 (m, 1 H, $CHMe_2$); 1.94–2.04 (m, 3 H, CHMe, 2 phosphetane CH); 2.49–2.57, 2.66–2.73 (2 m, 2 H, phosphetane $CH_2$); 7.29–7.41 (m, 3 H, phenyl-H); 7.62–7.69 (m, 2 , phenyl-H). $^{13}$C-NMR ($CDCl_3$, 50 MHz): δ19.20 (d, $J_{P,C}$5 Hz, $CH_3$); 20.42 (s, $CH_3$); 20.55 (d, $J_{P,C}$6.5 Hz, $CH_3$); 20.99 (d, $J_{P,C}$12.2 Hz, $CH_3$); 29.80 (d, $J_{P,C}$3.3 Hz, $CHMe_2$); 31.29 (d, $J_{P,C}$18.2 Hz, $CHMe_2$); 33.40 (d, $J_{P,C}$=Hz, phosphetane-$CH_2$); 35.51 (d, $^1J_{P,C}$8.7 Hz, phosphetane-CH), 37.77 (d, $^1J_{P,C}$32 5.8 Hz, phosphetane-CH); 128.05 (d, J6.0 Hz, m-C); 128–31 (s, p-C), 133.64 (d, J=17.6 Hz, o-C); 136.64 (d, J=32.6 Hz, ipso-C). $^{31}$P-NMR ($CDCl_3$, 162 MHz): δ19.92.

EXAMPLE 7

Bis[(2S,4S)-2,4-Diisopropyl-1-phenylphosphetano]-(1,5-cyclooctadiene)rhodium(I) tetrafluorborate A solution of (2S,4S)-2,4-diisopropyl-1-phenylphosphetane (1.0 g, 4.27 mmol) and $HBR_4·OEt_2$ (687 mg, 2.14 mmol) in THF (8 ml) was added under nitrogen via a syringe to [Rh)COD)(acac)] (662 mg, 2.14 mmol) within two minutes. The obtained orange solution was heated to reflux and after cooling to RT, diethyl ether (ca 10 ml) was added via a syringe. The complex crystallized spontaneously, and gave after filtering and drying a yield of 1.38 g (84.3%) of orange-yellow crystals. $^1$H-NMR ($CDCl_3$, 400 MHz); δ 0.54, 0.78, 1.16, 1.93 (4 d, J32 6.4 Hz, $CH_3$); 2.00–2.56 (m, COD-$CH_2$, 2 phosphetane-CH, 2 $CHMe_3$, phosphetane-$CH_2$), 2.72 (m, COD-$CH_2$), 5.10 ('br quart', COD-CH). 5.72 ('br tr', COD-CH), 7.14–7.82 (m, phenyl-H). $^{13}$C-NMR($CDCl_3$, 50 MHz); δ 16.87 ('tr', $CH_3$); 20.61 ('tr', $CH_3$); 21.55 ('s', $CH_3$); 25.51 ('tr', $CH_3$), 27.91 (COD-$CH_2$); 29.76 ('tr', $CHMe_2$); 30.61 ($CHME_2$); 39.98, 42.87 (2 m, phosphetane-CH); 95.41, 100.64 (2 m, COD-CH); 129.57 ('m', phenyl ipso-C); 128.58 ('tr'); 130.20(s); 131.06(broad m) (other phenyl-C). $^{31}$P-NMR ($CDCl_3$, 162 MHz); δ51.35 (d, $J_{P,RH}$144.5 Hz).

EXAMPLE 8

(3S,5S)-Heptane-3,5-diol

The distilled mixture of heptane-3,5-dione and diethyl malonate obtained from the reaction of diethyl malonate (317g) and propionic acid anhydride (515 g) (contains ca 150 g of the diketone) was dissolved in 300 ml of methanol and degassed by sparging with nitrogen for 20 minutes plus three following cycles of vacuum (5 min ca. 20 mbar) and stirring under nitrogen (5 min). To this solution was added the solution of the Ru-(S)-Tol-BINAP obtained from (S)-Tol-BINAP (247 mg, 0.36 mmol) and Ru (COD) (methallyl)$_2$ (106 mg, 0.33 mmol). The mixture was transferred under strict exclusion of air into a nitrogen-flushed 2 L Par hydrogenation bomb. After purging the bomb with hydrogen the hydrogenation was performed at 100° C./115 bar over night. The solvent was removed from the reaction mixture on a rotavapor, and the residue was distilled in vacuum over a 30 cm Vogreix column. Yield: 83 g, bp=140° C. at 26 mm, ee32 98% (chiral GC), the product solidifies on standing at RT. $^1$H-NMR ($CDCl_3$, 200 MHz): δ 0.90 (tr, 6 H, $^3$J=7.3 Hz, 2 $CH_3$); 1.34–1.66 (m, 6 H, 3 $CH_2$); 3.47 (br s, 2 H, OH), 3.80 ('pent', 2 H, CHOH) $^{13}$C-NMR ($CDCl_3$, 50 MHz): δ 10.01 ($CH_3$); 30.10 ($CH_2Me$); 41.40 ($CH_2$); 70.39 (CHOH).

EXAMPLE 9

(4S,6S)-4,6-Diethyl-2,2-dioxo-1,3,2-dioxathiane a) (4S,6S)-4,6-diethyl-2-oxo-1,3,2-dioxanthiane (cyclic sulfite). The product was obtained as described in Example 5a) from (3R,5R)-heptane-3,5-diol (11.0 g, 0.83 mol) and thionyl chloride (12.0 g, 0.101 mol). 14.9 yellow oil. $^1$H-NMR ($CDCl_3$, 50 MHz); δ 0.95–1.20 (m, 6 H, 2 $CH_3$); 1.50–1.85 (m 4 H), 1.90–2.15 (m, 2 H) ($CH_2$); 4.05–4.25 (m 1 H), 4.70–4.85 (m, 1 H) (2 CH).

b) (4S,6S)-4,6-dioxo-1,3,2-dioxanthiane (cyclic sulfate). The crude cyclic sulfite obtained from a) was dissolved in ethyl acetate (100 ml). To this solution was added $RuCl_3·xH_2O$(100 mg), ice (100 g), and $NaIO_4$ (25.7 g, 0.12 mol). The mixture was stirred rapidly, and within 1½ minutes the colour changed to yellow. The organic layer was decanted, and the aqueous layer was extracted with four portions of ethyl acetate (100 ml). To the vigorously stirred combined organic layers was added $Na_{SO3}$, and stirring was continued until the colour of the organic layer had disappeared almost completely (ca. 25 min). After drying ($Na_2SO_4$) and filtering the solvent was removed to leave the (4S,6S)-4,6-diethyl-2,2-dioxo-1,3,2-dioxathione as yellow oil Yield 15.1 (94%). $^1$H-NMR ($CDCl_3$, 200 MHz): δ 0.99 (tr, 6 H, J32 7.3 Hz, 2 $CH_3$); 1.59–1.89 (m, 2 H, $CH_2$); 1.89–2.12 (m, 4 H, 2 $CH_2$; $CH_3$); 4.75 (m, 2 H, 2 CH). $^{13}$C-NMR ($CDCl_3$, 50 MHz); δ 9.31 ($CH_3$), 26.82 ($CH_2$); 32.01 ($CH_2CH_3$), 85.21 (CH).

EXAMPLE 10

(2S,4S)-2,4-Diethyl-1-phenylphosphetane

In a 100 ml Schlenk flask a solution of lithium phenylphosphanide was prepared by the slow addition of n-BuLi (8 minutes, 2.5 n solution, 1.73 ml, 43.1 mmol) via a syringe to a solution of phenylphosphine (4.75 g, 43.1 mmol) in THF (60 ml) at 0° C.

A solution of the cyclic sulfate (4S,6S)-4,6-diethyl-2,2-dioxo-1,3,2-dioxathiane (8.80 g, 45.3 mmol, 5% excess) was made up in a Schlenk flask in absolute THF (400 ml), sparged with nitrogen for 30 minutes, and cooled to −78° C. The lithium phenylphosphanide solution was added to this solution via a syringe within 15 minutes. The pale yellow mixture was stirred at −78° C. for one more hour, and then the second portion of BuLi (2.5 n solution, 19 ml, 47.5 mmol) was added within 20 minutes to the reaction mixture. The mixture was allowed to warm up over night, and then the solvent was distilled off. To the residue was added water (100 mmol), and the ligand was the extracted from this mixture into pentane. After drying ($Na_2SO_4$) and removal of the solvent the residue was distilled in vacuum to give the ligand as colourless liquid, bp. 100° C. at 2 mbar. $^1$H-NMR ($CDCl_3$, 200 MHz); δ 0.60, 0.90 (2 tr, 3 H each, J=7.3 Hz, 2 $CH_3$), 1.75–1.95 (m, 3 H), 2.20–2.50 (m, 5 H) (2 $CH_2CH_3$, 2 phosphetane-CH, phosphetane-$CH_2$), 7.20–7.60 (m, 5 H, phenyl-H). C($CDCl_3$, 50 MHz); δ 11.92 (d, J4.7 Hz, $CH_3$), 12.90 (d, J=11.7 Hz, $CH_3$), 24.94 (d, J=4.3 Hz), 27.60 (d, J32 20.5 Hz, 2 $CH_2CH_3$), 31.62 (d, J32 0.9 Hz), 31.76 (d, J=2.5 Hz, 2 phosphetane CH), 34.67 (d, J=2.7 Hz, phosphetane $CH_2$), 127.69 (s), 127.97 (d, J=5.4 Hz), 132.10 (d, J=15.8 $H_2O$ (other phenyl C), 133.43 (d, J=32.9 Hz, phenyl ipso-C). $^{31}$P-NMR($CDCl_3$, 162 MHz): δ 18.74.

EXAMPLE 11

(R)-N-Acetyl-3-(2-naphthyl)alanine Methyl Ester

A solution of methyl (Z)-2acetamido-3-(2-naphthyl) propenoate (0.3 g, 1.11 mmol) and the catalyst (I) (7 mg, 0.011 mmol, 1.0 mol %) in degassed methanol (10 ml) was placed in a 50 ml Parr pressure reactor purged with nitrogen. The vessel was then purged with hydrogen (×3) and charged to 4.13 MPa (600 psi) of hydrogen. After stirring for 2 h, the solution was evaporated to give (R)-N-acetyl-3(2-naphthyl) alanine methyl ester (0.31 g, quantitative yield, 77.5% ee).

EXAMPLE 12

(R)-N-Acetylphenylalanine

A solution of α-acetamido-cinnamic acid (0.5 g, 2.44 mmol) and the catalyst (1) (16 mg, 0.024 mmol, 1.0 mol %) in degassed methanol (10 ml) was placed in a 50 ml Parr pressure reactor purged with nitrogen. The vessel was then purged with hydrogen (×3) and charged to 4.34 MPa (630 psi) of hydrogen. After stirring for 2 h, the solution was evaporated to give (R)-N-acetylphenylalanine (0.52 g, quantitative yield, 84.4% ee).

EXAMPLE 13

A solution of methyl 2-acetamidoacrylate (22 mg, 0.15 mmol) and the catalyst (I) (1 mg, 0.0015, 1 mol %) in degassed methanol (1 ml) was prepared under exclusion of oxygen in a GC-vial. The vial was placed in a 50 ml Parr reactor which was purged with hydrogen and charged to 3.41 MPa (500 psi). After hydrogenation of the mixture overnight, the solvent was evaporated to give the (R)-N-acetylalanine methyl ester (complete conversion, 62.8% ee).

EXAMPLE 14

2-Methylsuccinic Acid Dimethyl Ester

A solution of dimethyl itaconate (158 mg, 1 mmol) and the catalyst (I) (6 mg, 1 mmol, 1 mol %) in degassed methanol (10 ml) was prepared under exclusion of oxygen in a Schlenk flask. After hydrogenation of the mixture overnight at 3.41 MPa (500 psi), the solvent was evaporated to give the 2-methylsuccinic acid dimithyl ester (complete conversion, 11.7% ee, configuration unknown).

EXAMPLE 15

A solution of the catalyst (I) (1 mg, 0.0015 mmol) in degassed methanol (1 ml) was prepared under a nitrogen atmosphere and added to acetophenone (18 mg, 0.15 mmol) in a GC-vial. The vial was placed in a 50 reactor which was purged with hydrogen and charged to 3.41 MPa (500 psi). After stirring the mixture overnight, the solvent was evaporated and the residue submitted for analysis. (ca 5% conversion, 8.4% ee. configuration unknown).

Table 1 gives the results for Examples 13, 12, 14 and 15, respectively, i.e., using the rhodium-based catalyst (6), and also for the corresponding phospholane (7). As indicated above, results obtained according to the invention are invariably superior.

TABLE 1

| Substrate | (6) 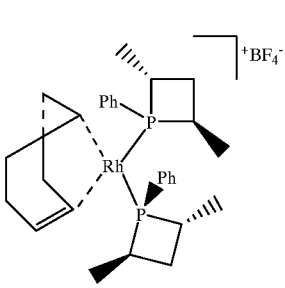 | | (7) 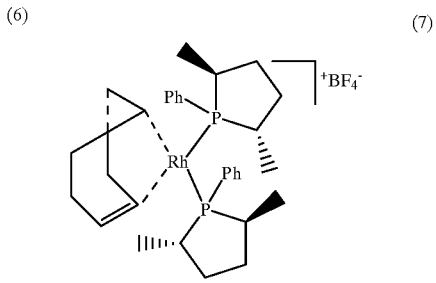 | |
|---|---|---|---|---|
| | conversion/% | ee/% | conversion/% | ee/% |
| Me-C(=O)-NH-C(=CH_2)-C(=O)-OMe | 100 | 62.8 | 100 | 26.1 |

TABLE 1-continued

|  | (6) | | (7) | |
|---|---|---|---|---|
| Substrate | conversion/% | ee/% | conversion/% | ee/% |
| 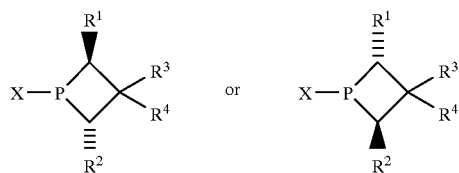 | 100 | 84.4 | 100 | 51.6 |
| 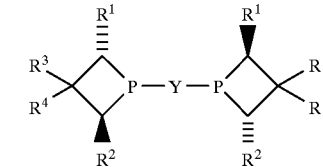 | 100 | 11.7 | 100 | 3.9 |
| 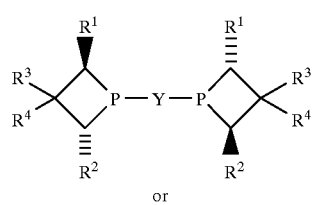 | ca. 5% | 8.4 | 0 | n/a |

I claim:

1. A chiral compound of the formula wherein $R^1$, $R^2$, $R^3$, and $R^4$ are each independently selected from the group consisting of H, alkyl, cycloalkyl, aryl, or alkaryl, provided that $R^1$ and $R^2$ are not both H; and X is any group capable of forming a stable bond to phosphorus.

2. A chiral compound of the formula wherein $R^1$, $R^2$, $R^3$, and $R^4$ are each independently selected from the group consisting of H, alkyl, cycloalkyl, aryl, or a alkaryl, provided that $R^1$ and $R^2$ are not both H; and wherein Y is any group capable of forming stable bonds to phosphorus.

3. The compound, according to claim 1, wherein X is alkyl or aryl.

4. The compound, according to claim 2, wherein Y is alkyl or aryl.

5. The compound, according to claim 1, wherein X is an organometallic radical.

6. The compound, according to claim 2, wherein Y is an organometallic radical.

7. The compound, according to claim 5, wherein X is ferrocenyl.

8. The compound, according to claim 6, wherein Y is ferrocenyl.

9. The compound, according to claim 1, wherein X is phenyl.

10. The compound, according to claim 2, wherein Y is 1,2-phenylene.

11. The compound, according to claim 2, wherein Y is $-(CH_2)_{1-6}-$.

12. The compound, according to claim 11, wherein Y is —CH$_2$—.

13. The compound, according to claim 1, wherein R$^1$=R$^2$.

14. The compound, according to claim 13, wherein R$^3$ and R$^4$ are each H.

15. A complex comprising a transition metal and a compound of claim 1.

16. The complex, according to claim 14, wherein the transition metal is selected from the group consisting if iridium, rhodium, and ruthenium.

17. A complex comprising a transition metal and a compound of claim 2.

18. The complex, according to claim 17, wherein the transition metal is selected from the group consisting of iridium, rhodium and ruthenium.

19. A method for producing an enantiomerically-enriched chiral compound from a prochiral starting material by an asymmetric reaction in the presence of a catalyst, said method comprising using as the catalyst a compound of claim 1.

20. A method for producing an enantiomerically-enriched chiral compound from a prochiral starting material by an asymmetric reaction in the presence of a catalyst, said method comprising using as the catalyst a complex of claim 14.

21. The method, according to claim 19, wherein said reaction is an asymmetric hydrogenation or hydroformylation.

22. The method, according to claim 20, wherein said reaction is an asymmetric hydrogenation or hydroformylation.

23. A method for producing an enantiomerically-enriched chiral compound from a prochiral starting material by an asymmetric reaction in the presence of a catalyst, said method comprising using as the catalyst a compound of claim 2.

24. A method for producing an enantiomerically-enriched chiral compound from a prochiral starting material by an asymmetric reaction in the presence of a catalyst, said method comprising using as the catalyst a complex of claim 17.

25. The method, according to claim 23, wherein said reaction is an asymmetric hydrogenation of hydroformylation.

26. The method, according to claim 24, wherein said reaction is an asymmetric hydrogenation or hydroformylation.

* * * * *

UNITED STATES PATENT AND TRADEMARK OFFICE
CERTIFICATE OF CORRECTION

PATENT NO. : 5,936,109

DATED : August 10, 1999

INVENTOR(S) : Ulrich Berens

It is certified that error appears in the above-identified patent and that said Letters Patent is hereby corrected as shown below:

Column 12, line 47: "aryl, or a alkaryl" should read --aryl, or alkaryl--.

Column 12, line 67: "$-(CH^2)_{1-6}-$." should read --$-(CH_2)_{1-6}-$.--.

Column 13, line 8: "according to claim 14" should read --according to claim 15--.

Column 13, line 9: "consisting if" should read --consisting of--.

Column 14, line 18: "hydrogenation of" should read --hydrogenation or--.

Signed and Sealed this

Ninth Day of May, 2000

*Attest:*

Q. TODD DICKINSON

*Attesting Officer*          *Director of Patents and Trademarks*

UNITED STATES PATENT AND TRADEMARK OFFICE
CERTIFICATE OF CORRECTION

PATENT NO. : 5,936,109
DATED : August 10, 1999
INVENTOR(S) : Ulrich Berens

It is certified that error appears in the above-identified patent and that said Letters Patent is hereby corrected as shown below:

Column 12, line 47, "II," should read --H,--.

Signed and Sealed this

Twelfth Day of December, 2000

Attest:

Q. TODD DICKINSON

*Attesting Officer*          *Director of Patents and Trademarks*